United States Patent
Watt et al.

(10) Patent No.: US 9,809,613 B2
(45) Date of Patent: Nov. 7, 2017

(54) METAL CATALYZED HYDROLYSIS OF CELLULOSE AND HEMICELLULOSE TO PRODUCE MONOMERIC CARBOHYDRATES FOR TRANSPORTATION FUEL AND ELECTRICAL PRODUCTION

(71) Applicants: Gerald D. Watt, Provo, UT (US); Richard K. Watt, Provo, UT (US)

(72) Inventors: Gerald D. Watt, Provo, UT (US); Richard K. Watt, Provo, UT (US)

(73) Assignee: Brigham Young University, Provo, UT (US)

( * ) Notice: Subject to any disclaimer, the term of this patent is extended or adjusted under 35 U.S.C. 154(b) by 0 days.

(21) Appl. No.: 15/101,828

(22) PCT Filed: Dec. 5, 2014

(86) PCT No.: PCT/US2014/068873
§ 371 (c)(1),
(2) Date: Jun. 30, 2016

(87) PCT Pub. No.: WO2015/085219
PCT Pub. Date: Jun. 11, 2015

(65) Prior Publication Data
US 2016/0311841 A1 Oct. 27, 2016

Related U.S. Application Data
(60) Provisional application No. 61/963,505, filed on Dec. 5, 2013.

(51) Int. Cl.
*C07H 3/02* (2006.01)
*C07H 1/08* (2006.01)
(Continued)

(52) U.S. Cl.
CPC .............. *C07H 3/02* (2013.01); *B01J 27/128* (2013.01); *B01J 27/26* (2013.01); *C07H 1/08* (2013.01);
(Continued)

(58) Field of Classification Search
CPC ....................................................... C07H 3/02
See application file for complete search history.

(56) References Cited

U.S. PATENT DOCUMENTS 3,607,438 A * 9/1971 Coffield .................. H01M 8/08
429/188
5,529,662 A  6/1996 Tan et al.
(Continued)

FOREIGN PATENT DOCUMENTS

CN    101509024    3/2012
WO    WO 2009/134816 A9    11/2009

OTHER PUBLICATIONS

Kobayashi et al, Synthesis of sugar alcohols by hydrolytic hydrogenation of cellulose over supported metal catalysts, 2011, Green Chemistry, 13, pp. 326-333.*
Kobayashi, H et al. Synthesis of Sugar Alcohols by Hydrolytic Hydrogenation of Cellulose Over Supported Metal Catalysts. Green Chemistry. Feb. 2011; Vo. 13, No. 2; pp. 326-333; abstract; p. 1, left column, first paragraph; p. 2, left column, second paragraph to p. 2, left column, fourth paragraphs; p. 3, right column, fourth paragraph.
(Continued)

*Primary Examiner* — Melvin C Mayes
*Assistant Examiner* — Stefanie Cohen
(74) *Attorney, Agent, or Firm* — Brinks Gilson & Lione; Ryan L. Marshall

(57) ABSTRACT

Methods and compositions for processing biomass using [Co(CN)5]3" are disclosed. The resulting products include monomeric carbohydrate units that can also be converted to basic alcohols, including ethanol, for a variety of uses including transportation fuels and the generation of electricity.

19 Claims, 2 Drawing Sheets

(51) Int. Cl.
*C12P 19/02* (2006.01)
*C12P 3/00* (2006.01)
*C12P 5/02* (2006.01)
*C12P 7/10* (2006.01)
*B01J 27/128* (2006.01)
*B01J 27/26* (2006.01)

(52) U.S. Cl.
CPC ................. *C12P 3/00* (2013.01); *C12P 5/023* (2013.01); *C12P 7/10* (2013.01); *C12P 19/02* (2013.01); *C12P 2201/00* (2013.01); *Y02E 50/16* (2013.01); *Y02E 50/17* (2013.01); *Y02E 50/343* (2013.01)

(56) References Cited

U.S. PATENT DOCUMENTS

| | | |
|---|---|---|
| 6,057,262 A | 5/2000 | Derbyshire et al. |
| 2013/0059354 A1 | 3/2013 | Borresen et al. |

OTHER PUBLICATIONS

Petrucci, O. Ferritin-Based Photo-Oxidation of Biomass for Nanoparticle Synthesis, Bioremediation, and Hydrogen Evolution. Brigham Young University Byu Scholars Archive. Dec. 1, 2013; p. 52, first paragraph; p. 60, fourth paragraph; p. 102, third paragraph; p. 145, first paragraph to p. 145, second paragraphs.
Search Report and Written Opinion of the International Searching Authority for PCT/US2014/068873, dated Mar. 18, 2015.

* cited by examiner

METAL CATALYZED HYDROLYSIS OF CELLULOSE AND HEMICELLULOSE TO PRODUCE MONOMERIC CARBOHYDRATES FOR TRANSPORTATION FUEL AND ELECTRICAL PRODUCTION

REFERENCE TO EARLIER FILED APPLICATIONS

This application is a 371 national phase of PCT/US2014/068873, filed Dec. 5, 2014, and claims priority to of U.S. Provisional Patent Application No. 61/963,505 filed on Dec. 5, 2013, which are incorporated by reference herein in their entirety.

FIELD OF THE TECHNOLOGY

The present disclosure generally relates to the field of biomass processing, and more particularly to the field of methods and compositions for breaking glycosidic bonds in cellulosic materials.

BACKGROUND

Cellulose is an abundant bio renewable polymer derived from biomass and is composed of individual monomer glucose units chemically bound together. Glucose monomers (but not cellulose, itself) are a valuable resource for producing biofuels such as ethanol and other liquid transportation fuels. Glucose monomers also can be used to efficiently produce electricity in an alkaline fuel cell. In order to capitalize on the promise of glucose to produce transportation fuels and to generate electricity for commercial use, it is essential to produce individual glucose units from the complex cellulose biopolymer. There exists in the art, therefore, an abundant need to find alternative, efficient means for breaking natural polymeric materials derived from biomass into monomeric units.

Once monomeric glucose and other monomeric carbohydrates are obtained, they are used to produce ethanol by known industrial processes to meet the needs of the transportation sector and reduce the use of petroleum products for this purpose. Generation of electricity from bio renewable glucose via the above process will make electrical generation from biomass a feasible process.

Glucose is currently used on a large scale to produce ethanol as part of a strategy to reduce dependence on petroleum as a transportation fuel. Furan-based fuels derived from carbohydrates are also being investigated for the same purpose. Recent developments also have shown that carbohydrates can be used to efficiently generate electricity using alkaline fuel cells. The promise of using abundant biomass components to replace petroleum for transportation purposes and for the production of electricity is clearly important. However, current agricultural methods for producing glucose for the above processes will soon face serious availability problems, as glucose use for fuel and electricity will compete with glucose for food production.

The production of ethanol from glucose for use as a transportation fuel will reduce dependence on fossil fuel-derived products for transportation. The major use will be in the transportation sector. In addition, using glucose derived from renewable biomass for large-scale commercial electrical production using glucose fuel cells will minimize greenhouse gas production, which in turn will lower atmospheric pollution.

The long-term solution for energy production from carbohydrates lies in converting cellulose and hemicellulose from biomass into their substituent monomeric units, typically carbohydrates. Both cellulose and hemicellulose are abundant in biomass. The problem is that no economically feasible processes are presently available for cellulose and hemicellulose conversion into their substituent carbohydrates. In order to capitalize on the promise of using biomass components for energy production, new and economically feasible methods must be found for producing carbohydrate monomers from cellulose and hemicellulose derived from biomass.

The U.S. National Renewable Energy Laboratory (NREL) is involved in a variety of programs to produce glucose from cellulose. For the most part, these programs focus on physical methods (steam explosion, fine grinding, etc.) to produce glucose from the cellulose polymer. In addition, they employ harsh chemical treatments such as high temperature and high acid and base hydrolysis procedures. While these processes currently produce glucose in varying amounts, they are currently not economically competitive, they require harsh conditions and chemicals, and significant decomposition of the product glucose occurs.

Other processes use enzymes derived from fungi, bacteria and yeast to degrade cellulose to glucose but they are slow and expensive processes and are currently not economically viable. Thus, although chemical means to break the glycosidic bond have been investigated, there remains a need in the art to obtain alternative processes that that efficiently produce glucose and other monomeric units from biomass.

SUMMARY OF THE INVENTION

In one aspect, a process for generating monomeric carbohydrates from a biomass feedstock is disclosed, including providing a biomass feedstock stream having one or more of cellulose, hemicellulose, amylose, maltodextrin, and mixtures of the same; and contacting the aqueous feed stock with a pentacyanocobaltate(II) anion catalyst having the formula $[Co(CN)_5]^{3-}$ to produce a product stream comprising at least one monomeric carbohydrate.

In some embodiments, the pentacyanocobaltate(II) anion is provided as metal or ammonium salt, wherein the metal if present excludes cesium. In some embodiments, the metal of the metal salt is selected from alkaline and alkaline earth metals. In some embodiments, the ammonium salt is $(NH_4^+)_3[Co(CN)_5]^{3-}$. In some embodiments, the catalyst is mounted to a solid support.

In some embodiments, the feedstock is provided in water (aqueous). In some embodiments, the feedstock is provided in dimethylformamide. In some embodiments, the feedstock is provided in dimethylsulfoxide.

In some embodiments, the catalyst is prepared in a non-aqueous solvent to form a dimer having the formula $\{[Co(CN)_5]^{3-}\}_2M_6^{6+}$ where M is cation. In some embodiments, M is selected from one of sodium and potassium. The solid can be isolated and added to an aqueous, biomass feedstock stream. In some embodiments, the non-aqueous solvent is methanol.

In some embodiments, the process also includes providing a ligand to the catalyst. In some embodiments, the ligand is anionic chloride.

In some embodiments, the catalyst breaks glycosidic bonds. In some embodiments, the glycosidic bond is selected from an α-1,4 glycosidic bond and a β-1, 4 glycosidic bond. In some embodiments, the glycosidic bond is an α-1,4 glycosidic bond. In some embodiments, the glycosidic bond is an β-1,4 glycosidic bond.

In some embodiments, the process also includes maintaining a pH greater than about 5. In some embodiments, the process includes maintaining a pH greater than about 7. In some embodiments, the process includes maintaining a pH greater than about 9.

In some embodiments, the process includes generating hydrogen gas. In some embodiments, the process includes maintaining a temperature of the aqueous feedstock at or below about 5° C.

In some embodiments, the process includes activating the biomass feedstock. In some embodiments, the biomass is derived from one or more of: switch grass, xylan, and mixtures of the same.

In some embodiments, the process also includes applying an electrical potential to the product stream. In some embodiments, the process is carried out under an inert atmosphere.

In some embodiments, the monomeric carbohydrate is selected from glucose, galactose, xylose, mannose, arabinose, rhamnose, and mixtures of the same. In some embodiments, the process also includes converting the one or more monomeric carbohydrates into ethanol. In some embodiments, the biomass feedstock is from pulp derived from biomass, waste material, recycled material, and combinations thereof. In some embodiments, the biomass feedstock is from short rotation forestry, industrial wood waste, forest residue, agricultural residue, energy crops, industrial wastewater, municipal wastewater, paper, cardboard, fabrics and combinations thereof.

In another aspect, a composition is disclosed which includes biomass having one or more of cellulose, hemicellulose, amylose, maltodextrin, and mixtures of the same; pentacyanocobaltate(II) anion catalyst having the formula $[Co(CN)_5]^{3-}$; and water.

In some embodiments, the pentacyanocobaltate(II) anion catalyst includes at least one counterion that is a metal or ammonium cation; wherein the metal if present excludes cesium. In some embodiments, the metal is selected from alkaline and alkaline earth metals. In some embodiments, the composition also includes a ligand. In some embodiments, the ligand is anionic chloride.

DETAILED DESCRIPTION

Definitions

Figure 1:
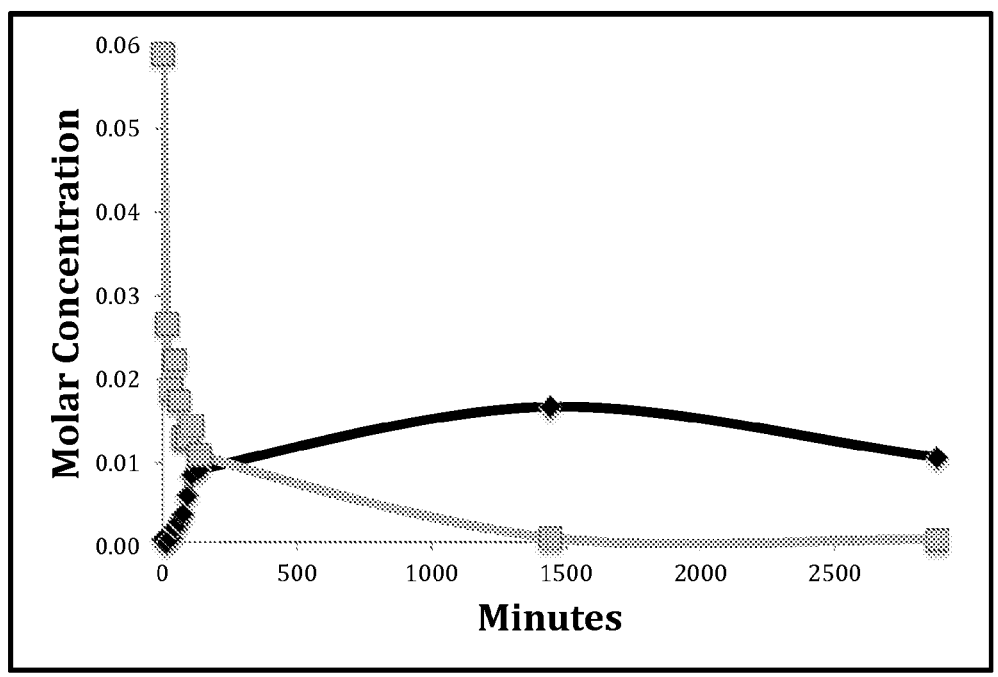
FIG. 1 is a plot of the molar concentration of cellobiose and glucose in a 2:1 ratio of $[CO(CN)^5]^{3-}$ with cellobiose per unit of time using one embodiment of the invention.

As used herein the specification, "a" or "an" may mean one or more. As used herein in the claim(s), when used in conjunction with the word "comprising", the words "a" or "an" may mean one or more than one. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or composition that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features.

Throughout this application, the term "about" is used to indicate that a value includes the standard deviation of error for the device or method being employed to determine the value.

The term "cellulosic biomass" as used herein refers to the fibrous, woody, and generally inedible portions of plants and in particular refers to cellulose-containing material that is from living or recently living organisms. The skilled artisan recognizes that cellulose is an organic compound with the formula $HO-[C_6H_{10}O_5]_n-H$, and constituted by polysaccharides comprising linear chains of several hundred to over ten thousand β-(1,4) linked D-glucose units, interconnected by hydrogen bond network.

The term "cellulosic biomass material" as used herein refers to matter that is comprised of cellulosic or any subcomponents of cellulose or starch or monosaccharides or disaccharides or polysaccharides. Cellulosic biomass starting materials that may be utilized include cellulose, starch, lignin, bagasse, grass, glucose, fructose, cellobiose and sucrose. Exemplary sources of cellulosic biomass include agricultural plant wastes, plant wastes from industrial processes (sawdust, paper pulp), or crops grown specifically for fuel production, such as switchgrass and poplar trees, for example.

The processes described herein readily produce glucose from cellobiose, hemicellulose and cellulose. The process described herein demonstrate that glucose and other monomeric units can be obtained from biomass such as cellulose using $[Co(CN)_5]^{3-}$.

The present invention describes a chemical process that carries out the breaking of the glycosidic bond that connects the individual glucose units in the cellulose polymer, thereby, producing monomeric glucose. The reaction occurs at room temperature and in water solution. The compound causing the cellulose-breakdown reaction is a metal complex formed between earth-abundant $Co^{2+}$ and NaCN by the reaction $Co^{2+}+5\ CN' \rightarrow [Co(CN)_5]^{3-}$. The reaction of $[Co(CN)_5]^{3-}$ with cellobiose, which is the simplest structure that contains a single glycosidic bond and is used as a model reaction for cellulose breakdown, produces nearly complete glycosidic bond breakage under the conditions used. The reaction with cellulose also causes glycosidic bond breakage in cellulose, producing glucose as a product and larger breakdown products of cellulose. In addition to glucose formation, the $[Co(CN)_5]^{3-}$ catalyst can concomitantly produces hydrogen gas ($H_2$), which is also a valuable potential fuel.

The process we describe uses inexpensive components, is carried out at room temperature in water solution and produces glucose without degradation. In addition the process that we describe is rapid and occurs within minutes. Under these conditions, the product should be easily separated or, very importantly, can be used without expensive separation and purification.

The invention does not require complex chemical processes, occurs under mild conditions and should easily be scaled to large-scale production.

Catalyst

Pentacyanocobaltate (II) is an $O_2$-sensitive, $d^7$ low-spin, inorganic free radical formed by Reaction 1: $Co^{2+}+5\ CN'\rightarrow[Co(CN)_5]^{3-}$. Because it is an anion, it may form ionic bonds with various cations including alkaline metals including lithium, sodium, potassium, rubidium, and francium ($Li^+$, $Na^+$, $K^+$, $Rb^+$, $Fr^+$); alkaline earth metals including beryllium, magnesium, calcium, strontium, barium, and radium ($Be^{2+}$, $Mg^{2+}$, $Ca^{2+}$, $Sr^{2+}$, $Ba^{2+}$, $Ra^{2+}$) transition metals and post-transition metals in their various oxidation states; and ammonium ions such as $NH_4^+$.

Also, because the catalyst is a anion, it may also be partially protonated with between 1 and 3 hydrogen atoms (Fr) depending upon the pH environment. As a result, the participation of any metal counterions may also be affected by the same pH environment and degree of protonation.

Because the catalyst is oxygen sensitive, reactions to degrade glycosidic bonds should be carried out under atmospheric conditions that exclude oxygen such as inert atmospheres (e.g. noble gases like argon or nitrogen) or reductive atmospheres like hydrogen.

Solvent

The disclosed reaction with the catalyst may be carried out in a solvent such as water, dimethylformamide (DMF), dimethylsulfoxide (DMSO), and mixtures of the same. In some embodiments, the solvent is water. In some embodiments, the solvent is DMF. In some embodiments, the solvent is DMSO.

Glycosidic Bonds and Biomass Materials

Glycosidic bonds are a type of covalent bond that joins a carbohydrate (sugar) molecule to another group, which may or may not be another carbohydrate. For example, a glycosidic bond is formed between the hemiacetal or hemiketal group of a saccharide (or a molecule derived from a saccharide) and the hydroxyl group of some compound such as an alcohol. A substance containing a glycosidic bond is a glycoside. Thus, a broad array of carbohydrates incorporated in biomass materials may be suitable for degradation into monomeric units by cleavage of the glycosidic bonds.

Cellulose is an organic compound with the formula $(C_6H_{10}O_5)_n$, a polysaccharide consisting of a linear chain of several hundred to many thousands of $\beta(1\rightarrow4)$ linked D-glucose units. Cellulose is an important structural component of the primary cell wall of green plants, many forms of algae and the oomycetes. Some species of bacteria secrete it to form biofilms. Cellulose is the most abundant organic polymer on Earth. For example, the cellulose content of cotton fiber is 90% and that of wood is 40-50%.

Cellobiose is the simplest complex carbohydrate that contains only one glycosidic bond. Cellobiose, therefore, can be used as a model complex carbohydrate for evaluating glycosidic bond breakage. Cellobiose consists of two glucose units connected by β-1-4 glycosidic bond.

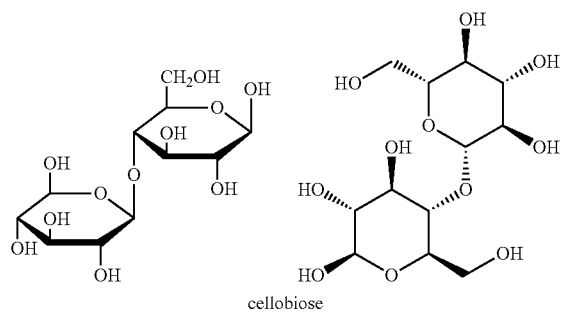

cellobiose

Hemicellulose (also known as polyose) is any of several heteropolymers (matrix polysaccharides), such as arabinoxylans, present along with cellulose in almost all plant cell walls. While cellulose is crystalline, strong, and resistant to hydrolysis, hemicellulose has a random, amorphous structure with little strength. A common polymeric subunit for hemicellulose is (xylose-β(1,4)-mannose-β(1,4)-glucose-α(1,3)-galactose).

The reaction of cellobiose with $[Co(CN)_5]^{3-}$ causes immediate breakage of the glycosidic bond under conditions of room temperature and in water solution. In general, the procedure used to break down cellobiose includes dissolving cellobiose and an appropriate amount of a cyanide source (e.g. NaCN) with cobalt$^{2+}$ (i.e. $NaCN/Co^{2+}$=5-6) in an anaerobic water solution followed by adding an anaerobic $Co^{2+}$ solution. The mixture is then vigorously stirred. Under these conditions, $[Co(CN)_5]^{3-}$ rapidly forms and initiates the breakage of the glycosidic bond in cellobiose, resulting in a rapid released of glucose.

A similar procedure is followed using hemicellulose and cellulose in place of cellobiose. In these latter cases, both are insoluble in water and it is necessary to conduct the reaction as a rapidly stirred suspension of the two insoluble polymers. As with cellobiose, very rapid release of glucose (from cellulose) and other sugars (from hemicellulose) is observed upon $[Co(CN)_5]^{3-}$ formation. However, in the case of cellulose, hydrogen gas evolution can occur simultaneously with glucose formation. Formation of glucose from cellulose was the desired reaction but the production of hydrogen gas was found to compete with glucose formation and lower its production. However, hydrogen gas is a valuable chemical product that can be used as a fuel for hydrogen-fuel cells to produce electricity and, while its formation detracts from glucose formation, its formation by this process is also a valuable product. Hemicellulose reacts in a similar manner as cellulose, but generally less hydrogen gas is produced. Alteration of conditions can be used to adjust the amount of the two products produced from cellulose and to favor the desired product for a given application.

Without wishing to be bound by any particular theory, it is believed that the reaction of the glycosidic bond in cellobiose follows a reactivity trend described in Reaction 2: $2[Co(CN)_5]^{3-}+ROH=[Co(CN)_5-OR]^{3-}+[Co(CN)_5-H]^{3-}$ (where R=H or an optionally substituted alkyl group).

Biomass Sources

In one embodiment, biomass feedstock to the process includes cellulose. Cellulose is a large renewable resource having a variety of attractive sources, such as residue from agricultural production or waste from forestry or forest products. Since cellulose cannot be digested by humans, using cellulose as a feedstock does not take from our food supply. Furthermore, cellulose can be a low cost waste type feedstock material which is converted herein to high value products and renewable, convenient, and cost-effective energy sources. In one embodiment, the feedstock to the process includes hemicellulose.

The cellulose containing feedstock may be derived from sources such as biomass, pulp derived from biomass, waste material, recycled material. Examples include short rotation forestry, industrial wood waste, forest residue, agricultural residue, energy crops, industrial wastewater, municipal wastewater, paper, cardboard, fabrics and combinations thereof. Multiple materials may be used as co-feedstocks. With respect to biomass, the feedstock may be whole biomass including lignin and hemicellulose, treated biomass where the cellulose is at least partially depolymerized, or where the ligin, hemicellulose, or both have been at least partially removed from the whole biomass.

The biomass source may from, for example, corn including corn stalk that is a good source of amylose.

Pretreatment of the feedstock may be performed in order to facilitate transporting and processing of the feedstock. Suitable pretreatment operations may include sizing, drying, grinding, hot water treatment, steam treatment, hydrolysis, pyrolysis, thermal treatment, chemical treatment, biological treatment, catalytic treatment, and combinations thereof. Sizing, grinding or drying may result in solid particles of a size that may be flowed or moved through a continuous process using a liquid or gas flow, or mechanical means. An example of a chemical treatment is mild acid hydrolysis, an example of catalytic treatment is catalytic hydrolysis, catalytic hydrogenation, or both, and an example of biological treatment is enzymatic hydrolysis. Hot water treatment, steam treatment, thermal treatment, chemical treatment, biological treatment, or catalytic treatment may result in lower molecular weight saccharides and depolymerized lignins that are more easily transported as compared to the untreated cellulose. Suitable pretreatment techniques are known in the art (see US 2002/0059991, incorporated herein by reference in its entirety).

EXAMPLES

Three types of cellulose samples were used: Two separate lots of Watman fibrous CF11 powdered cellulose and cotton cellulose fibers from Sigma. $CoCl_2 \cdot 6H_2O$ and NaCN were from Aldrich. All reactions utilizing $[Co(CN)_5]^{3-}$ were conducted under anaerobic conditions ($Ar$, $N_2$) in aqueous solution at a CN—/Co ratio of 5.0-6.0. The reactions with the various carbohydrates were initiated at 23 or 50° C. by first dissolving (suspending) the carbohydrate and NaCN in 1.0 mL of degassed water. The solution was vigorously stirred and $Co^{2+}$ (1-3 mL of 0.05-0.60 M) was added to form $[Co(CN)_5]^{3-}$. Samples were removed at various times and the glucose concentration was measured by mass spectrometry (Agilent LC/MSD TOF 6210), liquid chromatography (Agilent 1100 LC-RI) and by a glucose kit from Megazyme. Glucose, cellobiose, cellotriose and cellotetrose standards were run in 0.025 M NaCl to identify the MS and LC position of these and other oligo carbohydrates.

Cellobiose Reactivity

The relative proportions of cellobiose and glucose during the reaction of cellobiose with $[Co(CN)_5]^{3-}$ in aqueous solution at 50° C. is shown in FIG. 1. The initial ratio of $[Co(CN)_5]^{3-}$ to available glycosidic bonds in cellobiose is 2. The cellobiose concentration goes to zero and the glucose concentration reaches a maximum in 12 hours but only 15% of that expected from complete cellobiose hydrolysis is observed. These results suggest that glucose is initially bound to cobalt and then slowly released.

The anionic cobalt species were bound to an anion exchange resin, washed with water to remove any free glucose and eluted with 5.0 M NaCl. An additional 10-15% of the expected glucose from the initial cellobiose concentration was eluted. Running the reaction in 1.0 M NaCl increased glucose concentration 5-7 times that shown in FIG. 2 and supports the view that glucose is initially bound to cobalt. Infrared (IR) spectra of the evaporated reaction mixture showed strong IR bands due to cobalt-bound cyanide and other bands due to carbohydrate; some of the latter were shifted from the glucose control. Proton NMR showed slightly broadened carbohydrate resonances, some shifted from the glucose control. Mass spectrometry has not yet demonstrated the presence of a cobalt-glucose species, which is inferred from the above results. The results are consistent with nearly complete breakage of the glycosidic β-1-4 bond of cellobiose with formation of a cobalt-glucose species.

At exposure times greater than 12 hours, the cellobiose concentration increases slightly and the glucose concentration decreases, suggesting catalysis of the reverse reaction. This is confirmed by reacting $[Co(CN)_5]^{3-}$ with glucose and measuring (MS and LC) small amounts of cellobiose and trace amounts of larger oligosaccharides.

Cellulose Reactivity

The reaction of cellulose was observed by forming $[Co(CN)_5]^{3-}$ in an anaerobic aqueous suspension of rapidly stirred cellulose. Samples were removed for carbohydrate analysis and after a reaction interval of about 1-5 hours, the solution was centrifuged, the unreacted cellulose washed with water, dried and weighed. The amount of cellulose undergoing solubilization was dependent on the $[Co(CN)_5]^{3-}$/cellulose ratio, with low ratios (0.015 mMol Co/100 mg cellulose) giving 5-10% cellulose solubilization and higher ratios (1.2 mMol Co/100 mg cellulose) giving up to 35% solubilization. However, LC and MS analysis of the supernatant demonstrated that less than 1% glucose, less than 3% cellobiose, and only small amounts of other oligosaccharides were formed based on the initial cellulose loading, relative to a water control lacking $[Co(CN)_5]^{3-}$.

The concentration of these species does not account for the observed loss of cellulose, and it appears that glucose or smaller fragments of cellulose may be attached to cobalt as observed above. Some experiments show that the solid cellulose after reaction is a pale blue color and contains Co. This observation is consistent with Co attached to the cellulose polymer.

The low but variable levels of cellulose solubilization with Co/cellulose ratio were found to be partly due to hydrogen gas formation. Hydrogen gas formation in general increased at high Co/cellulose ratios but was lower at low ratios. The low conversion efficiency of cellulose into smaller carbohydrates was initially considered to be a consequence of hydrogen gas production, which inactivates $[Co(CN)_5]^{3-}$ by Reaction 3:

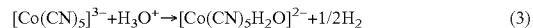

$$[Co(CN)_5]^{3-} + H_3O^+ \rightarrow [Co(CN)_5 H_2O]^{2-} + 1/2 H_2 \qquad (3)$$

It is known that large cations ($Cs^+$) and small particles catalyze Reaction (3) with formation of hydrogen gas. The suspended cellulose particles catalyze hydrogen gas formation, which inactivates $[Co(CN)_5]^{3-}$, and thereby limit the breaking of glycosidic bonds. Accordingly, in some embodiments, cesium counterions are excluded.

The unreactive cellulose from the above experiment was mixed with a second portion of $[Co(CN)_5]^{3-}$, and this particulate cellulose produced hydrogen gas but only about 1-5% of the cellulose mass was lost. This suggests that the cellulose samples that we have investigated consists of two forms: one at about 35% that reacts with $[Co(CN)_5]^{3-}$ and a second less than 35% that is unreactive.

Reactivity of Carboxy Methyl Cellulose (CMC)

$[Co(CN)_5]^{3-}$ was reacted with single-chain CMC, but no glucose or carboxy methyl glucose was formed. Only trace amounts of hydrogen gas were detected. The negatively charged carboxy methyl groups along the glucose chain may prevent the highly negative $[Co(CN)_5]^{3-}$ from approaching the glycosidic bond for cleavage.

α-1-4-Glycosidic Bond Reactivity

Figure 2:
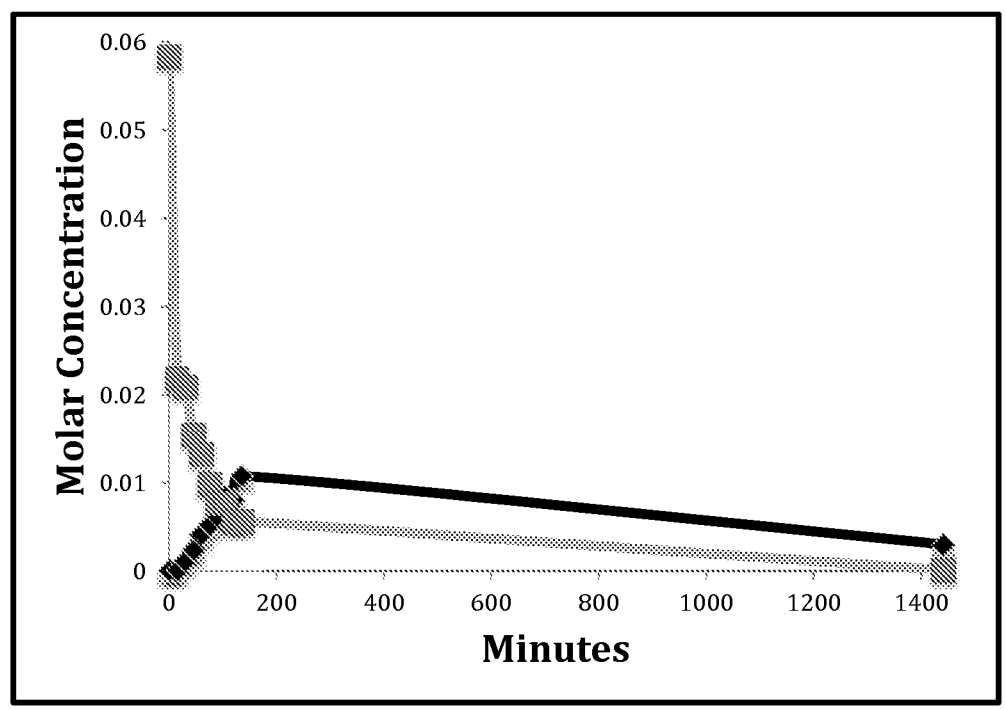
FIG. 2 is a plot of the observed molar concentration of maltose and glucose in a 2:1 ratio of $[Co(CN)^5]^{3-}$ with maltose per unit of time using one embodiment of the invention.

Maltose and lactose are disaccharides consisting of two glucose units and one unit each of glucose and galactose, respectively, connected by α-1-4-glycosidic bonds. Their structures are the opposite configuration to the β-1-4 glycosidic bond in cellobiose. As illustrated in FIG. 2, $[Co(CN)_5]^{3-}$ reacts with maltose, which disappears in about 30 min after which glucose begins to slowly form with no measurable hydrogen gas formation, but only less than 15% of the expected glucose is measured. A similar reaction occurs with lactose. The rate and amount of glucose formation is slightly greater than that in FIG. 1 for cellobiose.

Maltodextrin Reactivity

Maltodextrin is a smaller, water-soluble polymer formed from partial hydrolysis of amylose and consists of a mixture of small oligosaccharides. The mass spectra of the various components comprising maltodextrin disappeared in 30 minutes after reaction with $[Co(CN)_5]^{3-}$ but only small amounts of glucose and maltose were observed. No hydrogen gas was evolved. The particulate nature of cellulose and amylose, to a lesser extent, therefore, may catalyze hydrogen gas evolution.

Amylose Reactivity

Amylose is an insoluble glucose polymer made up of α-1-4-glycosidic bonds and unlike cellulose which contains compact and unreactive linear chains tightly twisted together, amylose has a branched and open structure. The reaction of insoluble amylose with $[Co(CN)_5]^{3-}$ formed a particle-free, clear solution in about 10 minutes at a $[Co(CN)_5]^{3-}$/amylose ratio of 1.2 mMol Co/100 mg amylose.

Amylose solubilization was also ratio dependent and was accompanied by some hydrogen gas evolution. Because amylose solubilization was more complete than with cellulose, however, the amount of hydrogen gas evolved was less, and the reaction was more efficient. Only small amounts of free glucose (~1%) and maltose (~2%) were formed, again suggesting that the products of solubilized amylose were attached to Co.

Switch Grass Reactivity

Preliminary studies of the reaction of $[Co(CN)_5]^3$ with finely powdered switch grass demonstrated that after about 2 hours, 25-30% of the original switch grass mass disappears (relative to a water control) and a dark brown cobalt-containing supernatant results. The loss of mass is consistent with $[Co(CN)_5]^{3-}$ reacting with the cellulosic and/or hemicellulosic components of switch grass forming cobalt-carbohydrate adducts.

The results demonstrate that both α- and β-1,4 glycosidic bonds in model compounds are broken by $[Co(CN)_5]^{3-}$ to form cobalt-bound monomeric carbohydrates with some or no hydrogen gas formation. The breaking of the glycosidic bond in naturally occurring cellulose also occurs but to a much smaller extent. It appears that the low extent of bond breaking in cellulose is a result of the hydrogen gas evolving reaction catalyzed by particulate cellulose and the inherent recalcitrance of greater than 35% of the cellulose to react with $[Co(CN)_5]^{3-}$.

The approach of using a metal-based complex for breaking the glycosidic bond in model compounds and in naturally occurring cellulose and amylose polymers is novel and has been shown to be feasible.

Ligand Participation

In some embodiments, the reaction includes addition of a ligand. Suitable ligands include those that are known to associate with cobalt complexes, including cobalt (II) complexes, for example chloride ($Cl^-$, $Br^-$, $NH_3$, and $CN^-$). Thus, in some reactions, chloride is added to the reaction such as sodium or potassium chloride. The ligand may be added as a ratio of from about 8 to 1 (ligand to catalyst), in some embodiments from about 7 to 1, in some embodiments from about 6 to 1, in some embodiments from about 5 to 1, in some embodiments from about 4 to 1, in some embodiments from about 3 to 1, in some embodiments from about 2 to 1, in some embodiments from about 1 to 1, and in some embodiments from about 0.5 to 1.

As described above, some reaction conditions result in concomitant production of hydrogen gas. This may be desirable for the providing an alternative fuel source. Hydrogen gas production may be less desirable if the monomeric carbohydrate is the desired product.

Inactive $[Co(CN)_5H_2O]^{2-}$ is easily regenerated to $[Co(CN)_5]^{3-}$ by electrochemical reduction at potentials near a pH 7.0 using a metallic electrode (for example Pt, Ag, stainless steel). The regenerated $[Co(CN)_5]^{3-}$ can then continue glycosidic bond breaking. This regeneration process detracts from the goal of cellulose breakdown, but the released hydrogen gas from the overall process can be recovered as a valuable byproduct and recycled to partially offset the electrical energy required for regeneration. In this process the $[Co(CN)_5H_2O]^{2-}/[Co(CN)_5]^{3-}$ redox couple functions in water as a hydrogen gas-evolving system catalyzed by particulate cellulose with a low over potential.

One skilled in the art will understand that the embodiment of the present invention as shown in the drawings and described above is exemplary only and not intended to be limiting. Embodiments have been shown and described for the purposes of illustrating the functional and structural principles of the present invention and is subject to change without departure from such principles. Therefore, this invention includes all modifications encompassed within the spirit and scope of the following statements and claims.

Statements (1) A process for generating monomeric carbohydrates from a biomass feedstock comprising: providing a biomass feedstock stream having one or more of cellulose, hemicellulose, amylose, maltodextrin, and mixtures of the same; and contacting the aqueous feed stock with a pentacyanocobaltate (II) anion catalyst having the formula $[Co(CN)_5]^{3-}$ to produce a product stream comprising at least one monomeric carbohydrate.

(2) The process of 1, wherein the pentacyanocobaltate(II) anion is provided as metal or ammonium salt, wherein the metal if present excludes cesium.

(3) The process of 2, wherein the metal of the metal salt is selected from alkaline and alkaline earth metals.

(4) The process of 2, wherein the ammonium salt is $(NH_4^+)_3[Co(CN)_5]^{3-}$.

(5) The process of any one of 1-4, further comprising providing a ligand to the catalyst.

(6) The process of 5, wherein the ligand is anionic chloride.

(7) The process of any one of 1-6, wherein the catalyst breaks glycosidic bonds.

(8) The process of 7, wherein the glycosidic bond is selected from an α-1,4 glycosidic bond and a β-1, 4 glycosidic bond.

(9) The process of 7, wherein the glycosidic bond is an α-1,4 glycosidic bond.

(10) The process of 7, wherein the glycosidic bond is an β-1,4 glycosidic bond.

(11) The process of any one of 1-10, further comprising maintaining a pH greater than about 5.

(12) The process of any one of 1-10, further comprising maintaining a pH greater than about 7.

(13) The process of any one of 1-10, further comprising maintaining a pH greater than about 9.

(14) The process of any one of 1-12, further comprising generating hydrogen gas.

(15) The process of any one of 1-14, further comprising maintaining a temperature of the aqueous feedstock at or below about 5° C.
(16) The process of any one of 1-15, further comprising activating the biomass feedstock.
(17) The process of any one of 1-16, wherein the biomass feedstock is derived from one or more of: switch grass, xylan, and mixtures of the same.
(18) The process of any one of 1-17, further comprising applying an electrical potential to the product stream.
(19) The process of any one of 1-18, wherein the process is carried out under an inert atmosphere.
(20) The process of any one of 1-19, wherein the monomeric carbohydrate is selected from glucose, galactose, xylose, mannose, arabinose, rhamnose, and mixtures of the same.
(21) The process of 20, further comprising converting the one or more monomeric carbohydrates into ethanol.
(22) The process of any one of 1-21, wherein the biomass feedstock is from pulp derived from biomass, waste material, recycled material, and combinations thereof.
(23) The process of any one of 1-21, wherein the biomass feedstock is from short rotation forestry, industrial wood waste, forest residue, agricultural residue, energy crops, industrial wastewater, municipal wastewater, paper, cardboard, fabrics and combinations thereof.
(24) A composition, comprising: biomass having one or more of cellulose, hemicellulose, amylose, maltodextrin, and mixtures of the same; pentacyanocobaltate(II) anion catalyst having the formula $[Co(CN)_5]^{3-}$.
(25) The composition of 24, further comprising water.
(26) The composition of any of 24 and 25, wherein the pentacyanocobaltate(II) anion catalyst includes at least one counterion that is a metal or ammonium cation; wherein the metal if present excludes cesium.
(27) The composition of 26, wherein the metal is selected from alkaline and alkaline earth metals.
(28) The composition of any of 24-27, further comprising a ligand.
(29) The composition of claim 28, wherein the ligand is anionic chloride

What is claimed is:
1. A process for generating monomeric carbohydrates from a biomass feedstock comprising:
   providing a biomass feedstock stream having one or more of cellulose, hemicellulose, amylose, maltodextrin, and mixtures of the same;
   contacting the aqueous feed stock with a pentacyanocobaltate(II) anion catalyst having the formula $[Co(CN)_5]^{3-}$ to produce a product stream comprising at least one monomeric carbohydrate.

2. The process of claim 1, wherein the pentacyanocobaltate(II) anion is provided as metal or ammonium salt, wherein the metal if present excludes cesium.
3. The process of claim 2, wherein the metal of the metal salt is selected from alkaline and alkaline earth metals.
4. The process of claim 2, wherein the ammonium salt is $(NH_4^+)_3[Co(CN)_5]^{3-}$.
5. The process of claim 1, further comprising providing a ligand to the catalyst.
6. The process of claim 5, wherein the ligand is anionic chloride.
7. The process of claim 1, further comprising maintaining a pH greater than about 5.
8. The process of claim 1, wherein the biomass is derived from one or more of: switch grass, xylan, and mixtures of the same.
9. The process of claim 1, further comprising applying an electrical potential to the product stream.
10. The process of claim 1, wherein the monomeric carbohydrate is selected from glucose, galactose, xylose, mannose, arabinose, rhamnose, and mixtures of the same.
11. The process of claim 10, further comprising converting the one or more saccharides into ethanol.
12. The process of claim 1, wherein the biomass feedstock is from pulp derived from biomass, waste material, recycled material, and combinations thereof.
13. The process of claim 1, wherein the biomass feedstock is from short rotation forestry, industrial wood waste, forest residue, agricultural residue, energy crops, industrial wastewater, municipal wastewater, paper, cardboard, fabrics and combinations thereof.
14. A composition, comprising:
   biomass having one or more of cellulose, hemicellulose, amylose, maltodextrin, and mixtures of the same;
   pentacyanocobaltate(II) anion catalyst having the formula $[Co(CN)_5]^{3-}$.
15. The composition of claim 14, further comprising water.
16. The composition of claim 14, wherein the pentacyanocobaltate(II) anion catalyst includes at least one counterion that is a metal or ammonium cation; wherein the metal if present excludes cesium.
17. The composition of claim 16, wherein the metal is selected from alkaline and alkaline earth metals.
18. The composition of claim 14, further comprising a ligand.
19. The composition of claim 18, wherein the ligand is anionic chloride.

* * * * *